US006482654B1

(12) United States Patent
Cromartie et al.

(10) Patent No.: US 6,482,654 B1
(45) Date of Patent: Nov. 19, 2002

(54) METHOD OF DETECTING SHIKIMIC ACID

(75) Inventors: Thomas Houston Cromartie, Albany; Nicholas David Polge, Rhonert Park, both of CA (US)

(73) Assignee: Syngenta Limited, Guildford (GB)

( * ) Notice: Subject to any disclaimer, the term of this patent is extended or adjusted under 35 U.S.C. 154(b) by 0 days.

(21) Appl. No.: 09/500,062

(22) Filed: Feb. 8, 2000

(51) Int. Cl.$^7$ ............................................. G01N 33/00
(52) U.S. Cl. ........................ 436/129; 436/63; 436/120; 422/68.1
(58) Field of Search ......................... 436/129, 63, 720; 422/68.1

(56) References Cited

U.S. PATENT DOCUMENTS 4,294,911 A * 10/1981 Guild .......................... 430/326

OTHER PUBLICATIONS

Bunton, C.A., Oxidation in Organic Chemistry—A Series of Monographs, vol. 5A, pp. 367–399, 1965.

Siehl, Daniel L., Herbicide Activity: Toxicology, Biochemistry and Molecular Biology, R.M. Roe et al., eds, IOS Press, 1997, pp. 47–65.

Millican, R.C., "Assay of Shikimic Acid", Methods in Enzymology, vol. 17A, pp. 352–354, 1970.

Gaitonde, M.K. et al., The Journal of Biological Chemistry, vol. 230, No. 1, pp. 1042–1050, Jan. 1958.

Martin, Roger F., et al., Analytical Biochemistry, vol. 47, pp. 562–574, 1972.

Singh, B.K. et al., Weed Technology, vol. 12, pp. 527–530, 1998.

\* cited by examiner

*Primary Examiner*—Jill Warden
*Assistant Examiner*—Sam P. Siefke
(74) *Attorney, Agent, or Firm*—William A. Teoli, Jr.

(57) ABSTRACT

The invention provides methods of detecting shikimic acid comprising the steps of: oxidizing shikimic acid with periodic acid or a reagent comprising periodate and periodic acid; adding a strong base to generate a chromophore; stabilizing the chromophore with sulfite; detecting the presence of the chromophore; and optionally quantifying the amount of the chromophore. The methods of the invention can be performed directly with tissue extracts, preferably plant tissue extracts.

19 Claims, No Drawings

METHOD OF DETECTING SHIKIMIC ACID

FIELD OF THE INVENTION

The present invention relates to methods for detection of shikimic acid and more particularly to methods capable of detecting shikimic acid in plant material.

BACKGROUND OF THE INVENTION

Shikimic acid is an important intermediate in the biosynthesis of the aromatic amino acids phenylalanine, tyrosine and tryptophan from D-glucose.

The herbicide glyphosate, N-(phosphonomethyl) glycine, inhibits the biosynthesis of aromatic amino acids which ultimately causes accumulation of shikimic acid in plants. Glyphosate is a potent inhibitor of 5-enolpyruvyl-shikimate-3-phosphate (EPSP) synthase, a key enzyme in the aromatic amino acid biosynthetic pathway. Glyphosate initially causes accumulation of shikimate-3-phosphate, the substrate of EPSP synthase, which is then hydrolyzed in the plant to shikimate. Detection of shikimic acid in plants can be used to determine whether a plant has been exposed to glyphosate and can also be used to determine whether plants are resistant to this herbicide.

Gaitonde and Gordon, J. Biol. Chem., vol. 230, no. 1, p. 1043–1050 discloses a method for quantifying shikimic acid wherein a solution of shikimic acid is oxidized by periodic acid, sodium hydroxide is added to form a yellow chromophore, and glycine is added to stabilize the color. The optical density of the solution is then measured within ten minutes of adding sodium hydroxide to the solution.

Millican, Methods in Enzymology, vol. 17A, p. 352–353, 1970 discloses a method of detecting shikimic acid wherein a solution containing shikimic acid is oxidized with periodate, and then is treated with arsenite. Thiobarbituric acid is added and the solution takes on a red color. The solution is then extracted with cyclohexanone. The clear upper cyclohexanone phase contains the red color and the optical density of the cyclohexanone phase is then determined.

Singh and Shaner, Weed Technology, vol. 12, p. 527–530, 1998 discloses a method of detecting shikimic acid in plant tissue wherein a test sample containing shikimic acid was oxidized with periodic acid. The sample was then mixed with sodium hydroxide, glycine was added and the optical density was read.

Siehl, in *Herbicide Activity: Toxicology, Biochemistry and Molecular Biology*, R. M. Roc et al., editors, IOS Press, 1997, p. 37–65, discloses an assay method for the enzyme DAHP wherein the enzyme is incubated in the presence of its substrates phosphoenolpyruvate, and erythrose-4-phosphate. The reaction is stopped by addition of periodic acid. Sodium sulfite is later added to reduce excess periodate. Thiobarbituric acid is then added, followed in ten minutes by dimethylsulfoxide. Absorbance at 549 nm is then determined.

SUMMARY OF THE INVENTION

The present invention provides a method of detecting shikimic acid in an aqueous solution comprising the steps of a) oxidizing shikimic acid with periodic acid or a reagent comprising periodate and periodic acid (periodic acid and the reagent are referred to collectively herein as periodate); b) adding a strong base to generate a chromophore; c) adding sulfite to stabilize the chromophore; d) detecting the presence of the chromophore; and optionally e) quantifying the amount of the chromophore. The presence of the chromophore signals the presence of shikimic acid in the aqueous solution The amount of chromophore correlates directly with the amount of shikimic acid in the aqueous solution. In a preferred embodiment of the present invention, steps b and c are performed at the same time with a mixture comprising sulfite and a strong base so that reduction of excess periodate and generation of a chromophore take place at the same time.

Applicants have discovered that the use of periodic acid and periodate provides a more rapid reaction time with shikimic acid than periodic acid alone, especially when the oxidation is carried out at temperatures above ambient room temperature.

Applicants have additionally found that use of sulfite to reduce excess periodic acid and periodate greatly improves the stability of the chromophore generated by oxidation of shikimic acid followed by addition of strong base.

Applicants' method can also be used to detect shikimic acid in tissues, preferably plant tissue. Thus, another aspect of the invention provides a method for detection of shikimic acid in a test sample comprising the steps of (a) treating the test sample with periodic acid or a reagent comprising periodate and periodic acid; (b) adding a strong base to the test sample to generate a chromophore; (c) stabilizing the chromophore with sulfite; (d) detecting the presence of the chromophore, and optionally (e) quantifying the amount of the chromophore. Preferably, steps b and c are performed at the same time with a mixture comprising sulfite and a strong base so that reduction of excess periodate and generation of a chromophore take place at the same time.

Unlike some prior methods of detecting shikimic acid, Applicant's methods can be used directly with tissue extracts. Suitable tissue extracts can be produced without grinding or prolonged reflux of the plant material. Further, unlike some other prior methods, Applicants' method provides a more stable chromophore such that the detection of the chromophore need not occur as soon as possible after quenching the periodic acid oxidation. The applicability of the method of the present invention to direct use with tissue samples, the ability to delay detection of the chromophore for up to at least one hour, and optional quantification of the chromophore produced make the present invention well suited for high throughput screening of tissue samples.

These and other aspects of the present invention are set out in the following detailed description of the invention.

DETAILED DESCRIPTION OF THE INVENTION

Shikimic acid is oxidized by periodic acid to give trans-aconitic acid and a dialdehyde. When excess periodic acid is removed by addition of sufficient sodium hydroxide to raise the pH above 10, upon standing an intense yellow color develops. Only shikimic acid, quinic acid and tryptophan have been found to produce a chromophore having a yellow color under alkaline conditions, after treatment with periodic acid. The formation of the yellow color from shikimic acid, which may be characteristic of the dialdehyde formed, is the basis of several methods for detecting shikimic acid. The chromophore that produces the yellow color is not stable and some methods employ a compound such as glycine to stabilize the color. Applicants have found that sulfite stabilizes the chromophore much better than known methods and provides a method that can be used directly with tissue samples.

The present invention provides a method of detecting shikimic acid in an aqueous solution comprising the steps of a) oxidizing shikimic acid with periodic acid or a reagent comprising periodate and periodic acid (referred to collectively herein as periodate); b) adding a strong base to generate a chromophore; c) adding sulfite to stabilize the chromophore; d) detecting the presence of the chromophore; and optionally e) quantifying the amount of the chromophore. The presence of the chromophore signals the presence of shikimic acid in the aqueous solution. The amount of chromophore directly correlates with the amount of shikimic acid in the aqueous solution. The aqueous solution can be known to contain shikimic acid, such as when a known amount is added to an aqueous solution to create a standard, or suspected to contain shikimic acid, such as a test sample.

Detection of shikimic acid in plants can be used to determine whether a plant has been exposed to the herbicide glyphosate and can also be used to determine whether plants are resistant to this herbicide. Thus, the methods of the present invention are useful in situations where detection and/or quantification of shikimic acid is desired. For example, the methods of the present invention can be used for screening plants or plant tissues or cells to determine resistance to the herbicide glyphosate, or for testing crop plants to d&termine if they have been exposed to glyphosate.

The methods of the present invention are conveniently performed in aqueous solution. The aqueous solution can be water or a mixture of water and a water miscible organic solvent. The methods of the invention are suitable for use with a variety of types of tissue, including plant, animal, and microorganism tissue. Preferably, the tissue is a plant tissue. When tissue samples are used, it is first necessary to extract the shikimic acid into a suitable solvent, such as a solution of water and a water miscible organic solvent and then, if necessary, to clarify the resulting solution.

Shikimic acid can be extracted from tissues using any suitable method. Applicants have found that shikimic acid can be easily and quantitatively extracted from plant tissue at room temperature by a solution comprised of water and a water miscible organic solvent. Preferably, the plant tissue has been previously frozen below about −4° C. The solution used to extract shikimic acid from the tissue can have a basic or acidic pH. The water miscible organic solvent can be any solvent in which shikimic acid is soluble, preferably a low molecular weight alcohol, more preferably isopropanol. The tissue is incubated in the extraction solution until all or a sufficient amount of shikimic acid has been extracted. Extraction is generally complete after about 24 hours, but is usually complete after 16 to 24 hours, or even sooner.

A preferred solution for extracting shikimic acid is a 2:1 (volume:volume) mixture of 0.05 M alkali metal hydroxide (in water) and isopropanol. Preferably, the alkali metal hydroxide is sodium hydroxide or potassium hydroxide.

In a preferred method for extracting shikimic acid from plant tissue, the tissue frozen below about −4° C. is cut into small pieces and immersed in a sufficient amount of a 2:1 (v:v) mixture of 0.05 M sodium hydroxide or potassium hydroxide (in water) and isopropanol. Generally, for convenience, 1 mL of extraction mixture is used for each 0.1 gm of plant tissue, but other extraction mixture: tissue ratios are also suitable. The extraction is allowed to proceed at room temperature until no additional shikimic acid is extracted into solution. The shikimic acid in many plant tissues is completely extracted by this procedure in 16–22 hours.

Aliquots of the extraction mixture can then be analyzed for the presence of shikimic acid in accordance with the method of the invention without additional manipulation, making this process convenient for the analysis of large numbers of samples. For example, the tissue extractions can be conducted on small amounts of plant tissue in 96-well, or similar, plastic plates from which aliquots can be removed with automated sample handling equipment for determination of the absorbance and thereby the amount of shikimic acid in the plant samples.

Oxidation of the shikimic acid can be done with periodic acid, or a reagent comprising periodic acid and periodate (periodate reagent). For ease of reference herein, periodic acid and the reagent comprising periodic acid and periodate will be referred to generally as periodate. Preferably, a reagent comprising periodic acid and periodate in a 1:1 ratio is used for oxidation. The reagent can prepared in water to be 0.5% (weight/volume) periodic acid and 0.5% (weight/volume) sodium meta-periodate. The periodate is added to an aqueous solution containing, or suspected of containing, shikimic acid. Sufficient periodate is added to the aqueous solution so there is a substantial molar excess of periodate over known or suspected amounts of shikimic acid in the aqueous solution.

Oxidation of the shikimic acid can be performed at ambient room temperature or at an elevated temperature. Preferably, the oxidation takes place at a temperature between 25 and 65° C., more preferably between 35 and 50° C. Applicants have found that oxidation of the shikimic acid is complete after about thirty to forty-five minutes at 37° C. When the oxidation takes place at ambient room temperature, the oxidation takes about three hours.

Oxidation of the shikimic acid is stopped or quenched by addition of a strong base to the aqueous solution which generates a chromophore, and sulfite is added to reduce excess periodate which stabilizes the chromophore. Preferably, a mixture comprising the strong base and sulfite is added to the aqueous solution to quench the reaction and stabilize the chromophore at the same time. However, it is possible to accomplish this step by adding the base and freshly prepared sulfite solution separately.

Preferably the base is a strong base such as a hydroxide, more preferably the base is an alkali metal hydroxide, such as sodium hydroxide or potassium hydroxide, most preferably sodium hydroxide. Sufficient base is added to make the aqueous solution alkaline to a pH above 10, preferably above 11. Preferably, the base is mixed with water or other solvent, more preferably a mixture of the base and water is used in the methods of the invention. The addition of base and sulfite to the aqueous solution produces a stabilized chromophore, the presence of which can be detected in the aqueous solution for up to about an hour after the addition of base and sulfite.

Sulfite is added to the aqueous solution, separately or in a mixture with a strong base, in an amount sufficient to stabilize the chromophore generated by addition of strong base to the completed periodate oxidation reaction. Sulfite is added to the aqueous solution so there is at least at much sulfite on a molar basis as periodate. Excess sulfite does not interfere with the method of the invention. Any soluble form of sulfite can be used in the method of the invention, such as the sodium or potassium salt, more preferably the sulfite is sodium sulfite. Preferably, the sulfite is mixed with water or other solvent, more preferably a mixture of sulfite and water is used in the methods of the invention.

The presence of the chromophore in the aqueous solution, which signals the presence of shikimic acid, can be detected by any suitable method such as measuring optical density at 382 nm using a spectrophotometer, or visual inspection of the aqueous solution for a yellow color. Optionally, the amount of chromophore in the test sample can be quantified, thereby providing the amount of shikimic acid in the aqueous solution. Quantification can be done by any suitable method, such as comparison with a shikimic acid standard prepared using the method of the present invention with known amounts of shikimic acid. In a preferred embodiment of the invention, the optical density of the aqueous solution is measured at 382 nm using a spectrophotometer, and the amount of chromophore determined by comparison with a shikimic acid standard generated using known amounts of shikimic acid and measured at 382 nm using a spectrophotometer.

In the performance of the methods of the invention, for detection of the chromophore, it is preferable to have an absorbance of at least 0.05 absorbance units (AU) for the untreated control plant test sample and an absorbance of less than 2.0 AU for the test sample with the greatest amount of shikimic acid/shikimate in order to obtain optimal results from spectrophotometric measurement of the chromophore. Applicants have found that most plants treated with a lethal amount of glyphosate accumulated shikimic acid/shikimate to a level such that 5–10 $\mu$L of an aqueous solution prepared from about 150 mg of leaf tissue ground in 8-fold (w/v) of 0.25N hydrochloric acid could be added to 250 $\mu$L of periodate reagent and water to give a volume of 0.5 ml. After reaction with the periodate reagent and quenching by 0.5 ml of a mixture comprising sulfite and sodium hydroxide, there was 1 ml of solution with an absorbance of about 1.8 AU, while an untreated control plant gave an absorbance of about 0.1 AU.

In a preferred embodiment of the invention, the method of the invention is used to determine the presence and/or levels of shikimic acid in an acidic aqueous extract of plant tissue. In this embodiment of the invention a test sample of a tissue, preferably a test sample comprised of an aqueous solution of a plant tissue prepared as described herein, is treated with periodic acid or a reagent comprising periodate and periodic acid to oxidize shikimic acid. A strong base is added to the test sample to generate a chromophore, and the chromophore is stabilized with sulfite. The presence of the chromophore is then detected which signals the presence of shikimic acid in the test sample. Optionally, the amount of chromophore in the test sample is quantified to provide the amount of shikimic acid in the test sample.

The ability to delay detection and/or quantification of the chromophore for up to one at least one hour and the ability to use tissue extracts without additional manipulation make the method of the invention well-suited for use in high throughput screening and other occasions where large numbers of samples are to be tested.

For example, the tissue extractions can be conducted on small amounts of plant tissue in 96-well, or similar, plastic plates from which aliquots can be removed with automated sample handling equipment for determination of the absorbance and the amount of shikimic acid in the plant samples can be determined by comparison of the absorbance with a shikimic acid standard.

EXAMPLES

Example 1

Background Absorbance of Reagents

250 $\mu$l of water, 250 $\mu$l of periodate reagent, 0.3 ml 1N NaOH and 0.2 ml of 0.056M $Na_2SO_3$ were mixed together and the absorbance was measured at 382 $\mu$m. Absorbance was 0.047 and did not drift significantly over five minutes. The 0.056M concentration of sodium sulfite was chosen to be equimolar with the periodate added.

The periodate reagent was prepared in water to be 0.5% by weight periodic acid and 0.5% by weight sodium metaperiodate.

Example 2

Detection of Shikimic acid

Ten $\mu$l samples of 2 mM shikimic acid were added to 240 $\mu$l of water. Then 250 $\mu$l of periodate reagent was added. After minutes at 37° C., the reactions were quenched with a) 0.3 ml of 1N NaOH followed by 0.2 ml of 0.056M sodium sulfite, or b) 0.5ml of a combined solution prepared by mixing 0.3 ml of 1N NaOH and 0.2 ml of 0.056M sodium sulfite (referred to as the combined solution). Absorbance (A) of the solution at 382 nm was read immediately, and then after 5, 30, and 60 minutes of standing at room temperature. Results averaged from 3 replicates shown in Table 1 demonstrate an increase in 382 nm absorbance in the presence of added shikimic acid.

Table 1

| Addition to Assay Solution | A(382) at T = 0 min | A(382) at T = 5 min | A(382) at T = 30 min | A(382) at T = 60 min |
| --- | --- | --- | --- | --- |
| NaOH then $Na_2SO_3$ | 0.949 | 0.949 | 0.941 | 0.924 |
| combined solution | 0.959 | 0.957 | 0.953 | 0.930 |

The addition of base followed by $Na_2SO_3$ provides a chromophore with excellent stability over 30 min and only about 3% loss in absorbance after 60 min while addition of the combined reagent provides slightly increased sensitivity and equivalent stability. The combined solution is stable at room temperature for approximately 12 hours, but additional testing may show it is stable for longer periods of time.

Preparation of Calibration Curve

The amount of 2 mM shikimic acid indicated for each entry in Table 2 was placed in 1.5 ml polypropylene micro test tubes with water to make 250 $\mu$l. Then 250 $\mu$l of periodate reagent was added, and the tubes were maintained at 37° C. for 30 min, at which time 0.5 ml of the combined NaOH/sulfite reagent was added. The absorbance at 382 nm of each of the resulting solutions was determined within 5 min, and the average of two replications is shown in column two of Table 2.

TABLE 2

| $\mu$l 2mM shikimate | A(382) with water only | A(382) with plant extract |
| --- | --- | --- |
| 0 | 0.066 | 0.095 |
| 2 | 0.218 | 0.266 |
| 4 | 0.409 | 0.479 |
| 6 | 0.575 | 0.664 |
| 10 | 0.944 | 1.028 |
| 14 | 1.243 | 1.320 |

*Lolium perrenne* was grown in soil in a greenhouse for 2–3 weeks until the plants reached the 3–4 leaf stage. The aerial parts of the plants were harvested, and were immediately placed in a freezer maintained at −80° C. For preparation of plant extracts, samples of about 1 gm of tissue were thawed and weighed. The tissue was frozen in liquid $N_2$ and ground to a fine powder with a mortar and pestle. Then a volume of 0.25 N HCl equal to 4 times the weight of tissue was added, and the slurry was ground for an additional 5 min. This material was centrifuged at 25,000×g for 15 min, and the supernatant was removed by pipette and kept in an amber glass vial.

The method used to prepare the calibration curve was repeated except that 5 μl of the untreated Lolium extract was added to each tube. Results are shown in the third column of Table 2. If these data are plotted as absorbance vs. shikimate added, two parallel straight lines are obtained. The data for the shikimate only study show that this assay procedure gives a direct correlation between shikimate present and the absorbance at 382 nm, at least up to an absorbance of about 1.25. The data for the study in which plant extract was added along with the shikimate demonstrates both that extracts of untreated *Lolium perrenne* contain a small amount of shikimate and that addition of a plant extract does not interfere with this chemical assay for shikimate.

What is claimed is:

1. A method of detecting shikimic acid in an aqueous solution comprising the steps of:
    a) oxidizing shikimic acid with periodic acid or a reagent comprising periodate and periodic acid;
    b) adding a strong base to generate a chromophore;
    c) stabilizing said chromophore with sulfite;
    d) detecting the presence of said chromophore; and
    optionally e) quantifying the amount of said chromophore.

2. The method of claim 1 wherein said strong base is sodium hydroxide.

3. The method of claim 1 wherein said sulfite is sodium sulfite.

4. The method of claim 1 wherein said steps b and c are performed at the same time with a mixture comprising sulfite and a strong base.

5. The method of claim 1 wherein step (a) is performed with a reagent comprising periodic acid and periodate.

6. The method of claim 5 wherein the reagent comprises periodic acid and periodate in a 1:1 ratio.

7. The method of claim 1 wherein the shikimic acid is oxidized at a temperature between 25 and 65° C.

8. The method of claim 1 wherein the shikimic acid is oxidized at a temperature between 35 and 50° C.

9. The method of claim 1 wherein the strong base is potassium hydroxide.

10. The method of claim 1 wherein the sulfite is potassium sulfite.

11. A method of detecting shikimic acid in a test sample comprising the steps of
    (a) treating a test sample with periodic acid or a reagent comprising periodate and periodic acid;
    (b) adding a strong base to said test sample to generate a chromophore;
    (c) stabilizing said chromophore with sulfite;
    (d) detecting the presence of said chromophore; and
    optionally (e) quantifying the amount of said chromophore.

12. The method of claim 11 wherein said strong base is sodium hydroxide.

13. The method of claim 11 wherein said test sample is a sample of plant tissue.

14. The method of claim 11 wherein said sulfite is sodium sulfite.

15. The method of claim 11 wherein said steps b and c are performed at the same time with a mixture of sulfite and strong base.

16. The method of claim 11 wherein step (a) is performed with a reagent comprising periodic acid and periodate.

17. The method of claim 16 wherein the reagent comprises periodic acid and periodate in a 1:1 ratio.

18. The method of claim 11 wherein the strong base is potassium hydroxide.

19. The method of claim 11 wherein the sulfite is potassium sulfite.

* * * * *